US012805719B2

(12) United States Patent
Clifton

(10) Patent No.: US 12,805,719 B2
(45) Date of Patent: Nov. 24, 2026

(54) OPHTHALMIC IMAGING SYSTEM AND METHOD FOR SUPPRESSING AN IMAGING ARTEFACT IN AN OPHTHALMIC IMAGE

(71) Applicant: Optos plc, Dunfermline (GB)

(72) Inventor: David Clifton, Dunfermline (GB)

(73) Assignee: Optos plc, Dunfermline (GB)

( * ) Notice: Subject to any disclaimer, the term of this patent is extended or adjusted under 35 U.S.C. 154(b) by 228 days.

(21) Appl. No.: 18/743,202

(22) Filed: Jun. 14, 2024

(65) Prior Publication Data

US 2024/0415385 A1 Dec. 19, 2024

(30) Foreign Application Priority Data

Jun. 14, 2023 (EP) .................................... 23179219

(51) Int. Cl.
*G06T 7/00* (2017.01)
*A61B 3/00* (2006.01)
(Continued)

(52) U.S. Cl.
CPC ............ *A61B 3/102* (2013.01); *A61B 3/0025* (2013.01); *A61B 3/14* (2013.01); *G06T 7/0012* (2013.01);
(Continued)

(58) Field of Classification Search
CPC ......... A61B 3/102; A61B 3/0025; A61B 3/14; A61B 3/13; G06T 7/0012;
(Continued)

(56) References Cited

U.S. PATENT DOCUMENTS 11,715,197 B2 * 8/2023 Song ....................... G06F 18/22 382/100
2019/0166298 A1 5/2019 Tasdizen et al.
(Continued)

FOREIGN PATENT DOCUMENTS

GB 2568924 A 6/2019
JP 2017-046976 A 3/2017
(Continued)

OTHER PUBLICATIONS

European Search Report for EP Patent Application No. 23179219.3, Issued on Nov. 16, 2023, 4 pages.
(Continued)

*Primary Examiner* — Han Hoang
(74) *Attorney, Agent, or Firm* — Faegre Drinker Biddle & Reath LLP

(57) ABSTRACT

Aspects of the present invention relate to a method of suppressing a banding artefact in an ophthalmic image of a patient's eye. The method comprises: partitioning the ophthalmic image into a plurality of segments that partially overlap each other, applying an image correction algorithm, which computes a discrete cosine transform of each segment of the plurality of segments to suppress the banding artefact in the plurality of segments removing at least part of the one or more overlapping regions from each segment to remove an artefact introduced by the image correction algorithm to generate a respective corrected segment; and combining the corrected segments to generate a corrected ophthalmic image that comprises less of the banding artefact than the ophthalmic image.

20 Claims, 8 Drawing Sheets

(51) Int. Cl.
*A61B 3/10* (2006.01)
*A61B 3/14* (2006.01)

(52) U.S. Cl.
CPC ............... *G06T 2207/10008* (2013.01); *G06T 2207/20024* (2013.01); *G06T 2207/20052* (2013.01)

(58) Field of Classification Search
CPC . G06T 2207/10008; G06T 2207/20024; G06T 2207/20052; G06T 5/80; G06T 2207/10101; G06T 12/30
See application file for complete search history.

(56) References Cited

U.S. PATENT DOCUMENTS

| | | | | |
|---|---|---|---|---|
| 2019/0223713 | A1 | 7/2019 | Uhlhorn et al. | |
| 2019/0269319 | A1* | 9/2019 | Shiba | A61B 3/102 |
| 2020/0320711 | A1 | 10/2020 | Song et al. | |
| 2021/0321142 | A1 | 10/2021 | Lin et al. | |
| 2022/0309622 | A1* | 9/2022 | Kiser | G06T 5/70 |

FOREIGN PATENT DOCUMENTS

| | | | | |
|---|---|---|---|---|
| JP | 2019-150405 | A | 9/2019 | |
| WO | WO-2021236061 | A1 * | 11/2021 | G06T 7/13 |

OTHER PUBLICATIONS

Intention to grant received for European Patent Application No. 23179219.3, mailed on Apr. 15, 2025, 6 pages.
Examination Report issued in related application IN 202414044991, Jun. 11, 2026, 9 pages.

* cited by examiner

OPHTHALMIC IMAGING SYSTEM AND METHOD FOR SUPPRESSING AN IMAGING ARTEFACT IN AN OPHTHALMIC IMAGE

CROSS-REFERENCE TO RELATED APPLICATION

This application claims priority to European Application No. 23179219.3, filed on Jun. 14, 2023, which is hereby incorporated by reference in its entirety for all purposes.

FIELD

The present disclosure relates to an ophthalmic imaging system and to a method for suppressing a banding artefact in an ophthalmic image. In particular, but not exclusively, the present disclosure relates to suppressing banding artefacts introduced into an ophthalmic image by a polygon scanning mirror in an ophthalmic imaging system.

BACKGROUND

Ophthalmic imaging devices such as scanning laser ophthalmoscopes (SLO) and optical coherence tomography (OCT) imaging systems typically comprise a light source and a scanning system. The scanning system scans light emitted by the light source over a target imaging area, such as a patient's retina by using one or more scanning mirrors to control the position of the imaging light beam.

One type of mirror that can be used in a scanning system is a polygon scanning mirror. The polygon scanning mirror comprises a polygonal mirror mounted on a rotating shaft. The polygonal mirror comprises reflective facets arranged in a polygon. As the polygon scanning mirror is rotated the light beam reflects off the facets such that the light beam is scanned over the target area. Polygon scanning mirrors can scan light quickly over an imaging target. As such, polygon scanning mirrors are often used to scan the beam of light linearly over a target area. For example, if the scan pattern is a series of parallel vertical lines then the polygon scanning mirror would scan the light beam linearly along the vertical lines over the target area and a scanning mirror such as a scanning galvanometer may be used to control the horizontal position of the light beam on the target area. The polygon scanning mirror and scanning galvanometer mirror may work in conjunction to form an X-Y scanning system that can be used to scan a light beam over the imaging target to generate an image of the target.

Banding is an optical artefact that can arise in images that use a polygon scanning mirror to scan the light beam over the imaging target. Banding artefacts may manifest in images as a series of dark and/or light bands occurring periodically in the image. In the example where the polygon scanning mirror scans the imaging beam vertically across the imaging target, banding typically presents as dark and/or light bands extending vertically across the resultant image. However, banding artefacts can take other forms such as in the form of horizontal lines.

Banding artefacts in images can be caused by several contributing factors. For example, imperfect optical components within scanning systems can introduce banding in images. This can include irregularities or imperfections in the polygon scanning mirror or wobbling of the polygon scanning mirror as it rotates which can cause variations in the angular position of the facets of the polygon mirror as the polygon scanning mirror rotates. These variations can cause the imaging beam to deviate from its intended scan pattern thereby leading to visible lines or banding in the resultant image. Furthermore, variations in the reflectivity of each of the reflective facets or mirrors on the polygon can cause variations in intensity of the light scanned across the target area. Banding can also be caused by non-uniform line spacing between the lines scanned by the polygon scanning mirror which can be introduced by imperfections in the horizontal scanning galvanometer.

Ultimately, whilst banding artefacts may manifest in images for a variety of reasons and in a variety of forms, the presence of banding artefacts in images captured by an imaging system detracts from the quality of the resultant image. This can make it difficult for a clinician to visualise or assess the severity of pathologies within a resultant image if the image is a medical image of tissue such as an ophthalmic image of a retina. It is therefore desirable to minimise or eradicate banding from images to improve the quality of images captured by an imaging system having a polygon scanning mirror.

Banding in images can be suppressed by using high quality optical components within the imaging system. For example, using high quality reflective facets on the polygon can reduce variations in the reflectivity of each facet. However, high quality optical components can be very expensive which increases the overall cost of the imaging system. Furthermore, dampening vibrations within the imaging system can also help reduce the presence of banding in images captured by the imaging system although this can be challenging due to the inherent vibrations associated with the rotating polygon scanning mirror.

SUMMARY

There is described in the following a method of suppressing a banding artefact in an image of an imaging target, the method comprising: partitioning the image of the imaging target into a plurality of segments that partially overlap each other, wherein each segment of the plurality of segments comprises one or more overlapping regions, wherein each overlapping region is a region of overlap of the segment with a respective adjacent segment of the plurality of segments, applying an image correction algorithm, which computes a discrete cosine transform of each segment of the plurality of segments, to suppress the banding artefact in the plurality of segments; removing at least part of the one or more overlapping regions from each segment of the plurality of segments to remove an edge effect or artefact introduced by the image correction algorithm, to generate a respective corrected segment; and combining each of the corrected segments to generate a corrected image of the imaging target that comprises less of the banding artefact than the image.

There is provided, in accordance with a first example aspect herein, a method of suppressing a banding artefact, for example a periodic line artefact, in an ophthalmic image of a patient's eye, the method comprising: partitioning the ophthalmic image into a plurality of segments that partially overlap each other, wherein each segment of the plurality of segments comprises one or more overlapping regions, wherein each overlapping region is a region of overlap of the segment with a respective adjacent segment of the plurality of segments; applying an image correction algorithm, which computes a discrete cosine transform of each segment of the plurality of segments, to suppress the banding artefact in the plurality of segments; removing at least part of the one or more overlapping regions from each segment of the plurality of segments to remove an artefact introduced by the image correction algorithm, to generate a respective corrected segment; and combining the corrected segments to generate a corrected ophthalmic image that comprises less of the banding artefact than the ophthalmic image. The method and any of its example embodiments described in the following may be implemented (performed) by a computer, The method may comprise performing filtering in a frequency domain, after the discrete cosine transform has been computed, to remove at least one of low frequency signals and high frequency signals from each of the segments. Furthermore, performing filtering may comprise removing discrete cosine transform coefficients having an absolute value equal to or above a threshold value. For example, the threshold value may be an integer value such as 1, 2, 3 or greater. Removing discrete cosine transform coefficients having an absolute value equal to or above the threshold value may comprise setting the coefficients equal to or above the threshold value to zero.

Additionally or alternatively, the method may comprise applying a window function to the computed discrete cosine transform of each segment. The window function may be applied to window a bin in the discrete cosine transform of each segment, which bin corresponds to a spatial frequency of the banding artefact, to attenuate the banding artefact in the discrete cosine transform of each segment.

The window function may comprise a secondary component for filtering a second frequency corresponding to a harmonic of the frequency of the banding artefact. The secondary component may be applied to window a bin in the discrete cosine transform of each segment corresponding to the secondary frequency. The secondary frequency may be a multiple of the frequency of the frequency of the banding artefact. In an example embodiment the window function may be a Hanning window filter.

Optionally, the image correction algorithm may comprise computing, for each segment of the plurality of segments, a respective inverse discrete cosine transform of the segment after the discrete cosine transform has been computed for the segment.

The method may comprise combining the corrected segments to generate the corrected ophthalmic image. Combining the corrected segments may comprise blending a peripheral region of a first corrected segment of the corrected segments with a peripheral region of an adjacent corrected segment of the corrected segments. Blending a peripheral region of the first corrected segment with a peripheral region of the adjacent corrected segment may comprise aligning one or more features present in both the first corrected segment and the adjacent segment such that the one or more features are overlaid each other in the corrected image such that the join between the first corrected segment and the adjacent corrected segment is not visible.

There is provided, in accordance with a second example aspect herein, a computer program comprising computer-readable instructions which, when executed by a processor, cause the processor to perform a method according to the first example aspect or at least one of the example embodiments thereof set out above. The computer program may be stored on a non-transitory computer-readable storage medium or carried by a signal.

According to a third example aspect herein, there is provided an ophthalmic imaging system for imaging a patient's eye, the imaging system comprising: a light source arranged to emit a light beam; a scanning system comprising a polygon scanning mirror, wherein the polygon scanning mirror is arranged to scan the light beam over a region of the patient's eye, a photodetector optically coupled to the scanning system, wherein the photodetector is configured to generate a detection signal based on light reflected by the patient's eye; and data processing hardware or a processor configured to receive the detection signal from the photodetector and generate, based on the received detection signal, an ophthalmic image of the patient's eye, wherein the ophthalmic image comprises a banding artefact; wherein the data processing hardware is further configured to: partition the ophthalmic image into a plurality of segments that partially overlap each other, wherein each segment of the plurality of segments comprises one or more overlapping regions, wherein each overlapping region is a region of overlap of the segment with a respective adjacent segment of the plurality of segments; apply an image correction algorithm, which computes a discrete cosine transform of each segment of the plurality of segments, to suppress the banding artefact in the plurality of segments; remove at least part of the one or more overlapping regions from each segment of the plurality of segments to remove an artefact introduced by the image correction algorithm, to generate a corrected segment; and combine each of the corrected segments to generate a corrected ophthalmic image that comprises less of the banding artefact than the ophthalmic image.

The ophthalmic imaging system may be a scanning laser ophthalmoscope (SLO) imaging system or an optical coherence tomography (OCT) imaging system. The OCT imaging system may be, for example, a swept-source OCT, spectral-domain OCT, or Fourier domain OCT imaging system.

In an embodiment the data processing hardware may be further configured to perform filtering in a frequency domain, after the discrete cosine transform has been computed, to remove at least one of low frequency signals and high frequency signals from each of the segments. Removing or filtering at least one of the low frequency signals and the high frequency signals may comprise removing discrete cosine transform coefficients having an absolute value equal to or above a threshold value from each of the partially overlapping segments. Removing the discrete cosine transform coefficients having an absolute value equal to or above the threshold value may comprise setting the discrete cosine transform coefficients to zero.

Additionally or alternatively, the data processing hardware may be further configured to apply a window function to the computed discrete cosine transform of each segment. The window function may be applied to window a bin in the discrete cosine transform of each segment which bin corresponds to a spatial frequency of the banding artefact, to attenuate the banding artefact in the discrete cosine transform of each segment. The window function may comprise a secondary component for filtering a second frequency corresponding to a harmonic of the frequency of the banding artefact. The secondary component may be applied to window a bin in the discrete cosine transform of each segment corresponding to the secondary frequency of the harmonic. The window function may be a Hanning window.

Optionally, applying the image correction algorithm may further comprise computing for each segment of the plurality of segments, a respective inverse discrete cosine transform of the segment after the discrete cosine transform has been computed for each of the partially overlapping segments.

Optionally, combining the corrected segments to generate the corrected ophthalmic image may comprise blending a peripheral region of a first corrected segment of the corrected segments with a peripheral region of an adjacent corrected segment of the corrected segments.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

DETAILED DESCRIPTION

In view of the background above, the inventor has devised an ophthalmic imaging system for imaging a patient's eye which utilises a scanning system comprising a polygon scanning mirror for scanning a beam of light across a patient's eye to generate ophthalmic images of the patient's eye. The ophthalmic imaging system comprises a control module or data processing hardware arranged to apply an image correction algorithm to uncorrected ophthalmic images that contain banding artefacts to remove or suppress the banding artefacts present in the ophthalmic images. Removing or suppressing the banding artefacts in the ophthalmic images may comprise partitioning the ophthalmic image into partially overlapping segments, applying an image correction or an artefact suppression algorithm to each overlapping segment, cropping or removing overlapping regions of each of the partially overlapping segments and recombining the cropped segments to generate a corrected ophthalmic image that contains less of the banding artefact than the uncorrected image.

The use of data processing hardware arranged to apply an image correction algorithm to an uncorrected ophthalmic image that contains a banding artefact beneficially removes or suppresses banding artefacts from ophthalmic images thereby improving the image quality of images acquired by the ophthalmic imaging system. Banding artefacts in an ophthalmic image detract from the quality of the image and it is therefore beneficial to remove and/or suppress the banding artefacts present in images captured by the ophthalmic imaging system. The banding artefacts may be, for example, periodic line artefacts.

Partitioning an uncorrected image into partially overlapping segments and applying an image correction algorithm to each of the overlapping segments allows the banding artefact to be suppressed in each segment and any residual edge effects or edge artefacts introduced by the image correction algorithm are typically contained within the overlapping regions of the overlapping segments. Advantageously, the overlapping regions of each segment may be removed such that the central portion of each segment can be combined to create a corrected image thereby removing edge effects from the corrected image and only using the central portion of each corrected segment to generate the corrected image.

Figure 1:
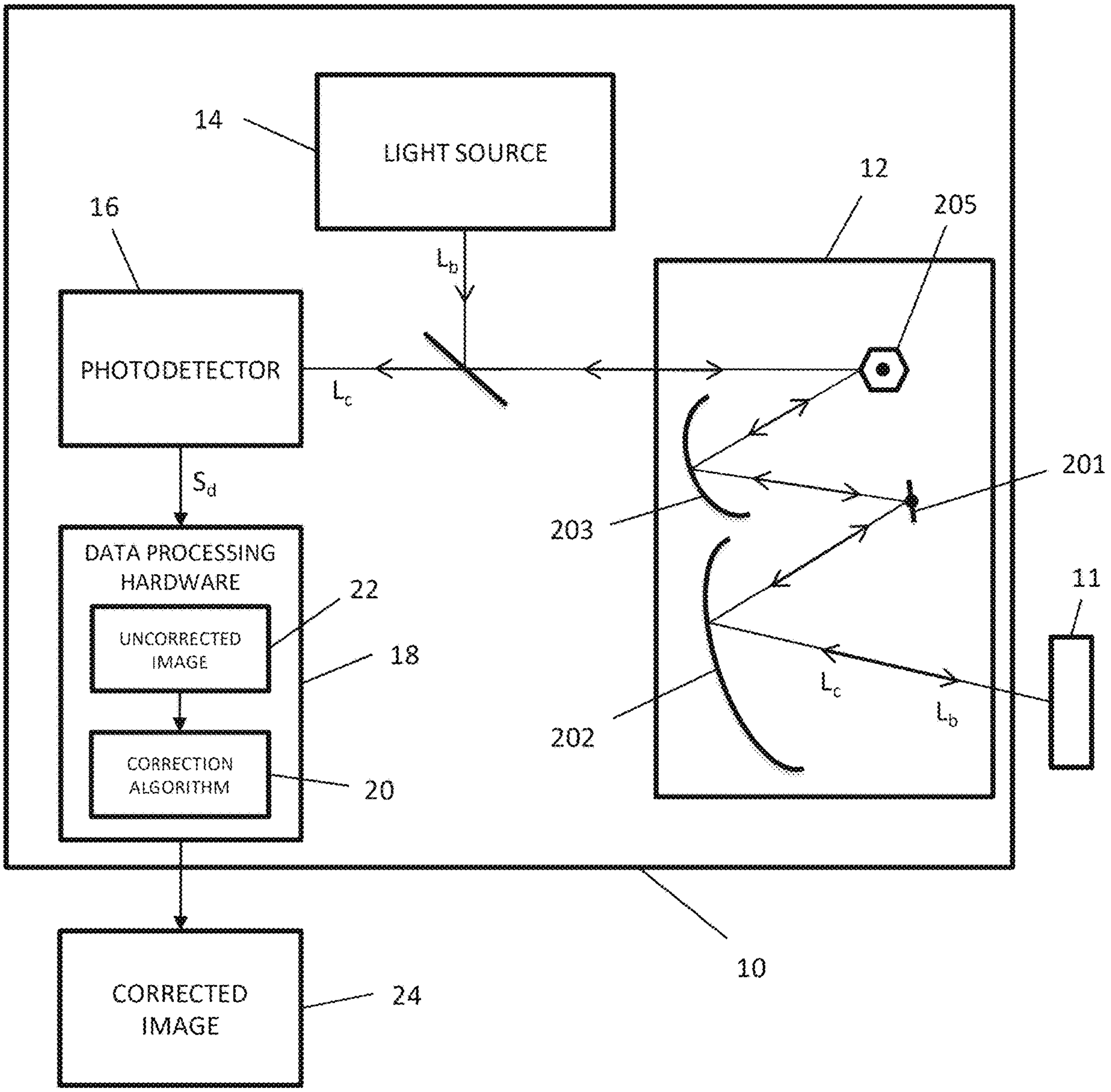
FIG. 1 is a schematic illustration of an imaging system comprising a polygon scanning mirror according to an example embodiment herein.

FIG. 1 shows an imaging system 10 for acquiring images of an imaging target 11. The imaging system 10 may be a medical imaging system, such as an ophthalmic imaging system, and the imaging target 11 may be biological tissue, for example, a patient's eye, such that the ophthalmic imaging system is arranged to capture ophthalmic images of the patient's eye. The imaging system 10 may be, for example, a scanning laser ophthalmoscope (SLO) imaging system or an optical coherence tomography (OCT) imaging system such as a swept-source OCT or spectral domain OCT imaging system. The imaging system 10 comprises a light source 14 such as a laser or a super luminescent diode (SLD) arranged to emit a light beam $L_b$ towards the scanning system 12 within the imaging system 10. The scanning system 12 is arranged to convey the light beam $L_b$ from the light source 14 to the imaging target 11 and to scan the light beam $L_b$ over the area of the imaging target 11 that is to be imaged.

Further, the scanning system 12 is arranged to collect light $L_c$ that has been reflected or scattered by the imaging target 11 during a scan and to convey the collected light $L_c$ to a photodetector 16 within the imaging system 10. The photodetector 16 is arranged to detect collected light $L_c$ such that image processing hardware (not shown) within the data processing hardware 18 can generate an image of the imaging target 11, based on the detection signal $S_d$, using well known data processing techniques. The image generated by the data processing hardware 18 may be an uncorrected ophthalmic image 22 of the imaging target 11 if the imaging target 11 is an eye. The uncorrected image 22 generated by the data processing hardware 18 comprises a banding artefact introduced by the polygon scanning mirror as discussed in further detail below.

The scanning system 12 may, as in the present example embodiment, include an arrangement of optical components as illustrated schematically in FIG. 1. The scanning system 12 of FIG. 1 comprises a first scanning element 201 and a first curved mirror 202. The scanning system 12 may, as in the present example, further comprise a second curved mirror 203 (also referred to herein as a "slit mirror") and a second scanning element in the form of a polygon scanning mirror 205. The first scanning element 201 may be a scanning galvanometer mirror arranged to scan the light beam $L_b$ horizontally across the imaging target 11. The second scanning element is a polygon scanning mirror 205 arranged to scan the light beam $L_b$ vertically across the imaging target 11. The polygon scanning mirror 205 comprises reflective facets arranged in a polygon. The polygon scanning mirror may comprise sixteen equally dimensioned reflective facets arranged in a polygonal shape. The location on the imaging target 11 that the light beam $L_b$ is scanned by the first and second scanning elements 201, 205 may be controlled by a scanning system controller (not shown).

During operation of the scanning system 12, the light beam $L_b$ emitted from the light source 14 enters the scanning system 12 and is focussed onto the polygon scanning mirror 205 by a lens (not shown). The light beam $L_b$ received by the polygon scanning mirror 205 is then reflected, in sequence, by the polygon scanning mirror 205, the second curved mirror 203, the first scanning element 201 and the first curved mirror 202, before being incident on the imaging target 11. The imaging target 11 may take the form of a region of a retina of an eye in the present example embodiment, although this form of imaging target 11 is given by way of an example only. The return light, which has been scattered by the illuminated region of the imaging target 11, for example the retina of the eye, follows the same optical path through the scanning system 12 as the line of light $L_b$ that is incident on the imaging target 11 but in reverse order, and exits the scanning system 12 as the collected light $L_c$, comprising the optical aberration or banding artefact caused by the polygon scanning mirror 205. The collected light $L_c$ is received by the photodetector 16.

The first curved mirror 202 and the second curved mirror 203 may, as in the present example embodiment, be a spheroidal mirror and an ellipsoidal mirror, respectively, each having a first focal point and a conjugate second focal point. The first scanning element 201 is located at the first focal point of the first curved mirror 202 and the imaging target 11 is located at the second focal point of the first curved mirror 202. Where the imaging target 11 is a portion of a retina of an eye 210 the pupil of the eye is located at the second focal point of the first curved mirror 202 such that the light beam $L_b$ is scanned across a region of the retina of the eye during the scan. The second polygon scanning mirror 205 is located at the first focal point of the second curved mirror 203, and the first scanning element 201 is located at the second focal point of the second curved mirror 203. However, the second curved mirror 203 (the ellipsoidal mirror in the present example embodiment) may be any reflective component having an aspherical reflective surface, such as a shape of a conical section like a parabola or hyperboloid, or may, more generally, have a shape described by one or more polynomial functions of two variables.

The collected light $L_c$ received by the photodetector 16 comprises a periodic optical artefact or banding artefact that is introduced into the collected light $L_c$ by the polygon scanning mirror 205. The banding artefact may have been introduced by the polygon scanning mirror 205 as a result of imperfections and/or defects in the polygon scanning mirror 205 or due to non-uniform scan line spacing. For example, the banding artefact may vary sinusoidally with a period of sixteen pixels in an embodiment where the polygon scanning mirror comprises sixteen reflective facets. The banding artefact may be caused by variability in the reflectiveness of each of the reflective facets in the polygon scanning mirror 205 thereby causing periodic variations in the intensity of light scanned across the imaging target 11.

The data processing hardware 18 receives the detection signal $S_d$ from the photodetector 16 and generates an image of the imaging target 11. The image generated by the data processing hardware 18 is an uncorrected image 22 which includes the optical aberration or banding artefact that was introduced into the collected light $L_c$ by the polygon scanning mirror 205 which detracts from the quality of the image. The data processing hardware 18 comprises an image correction algorithm 20 that is executable by the data processing hardware 18 to remove or reduce the amount of aberration or banding artefact in the generated uncorrected image 22. Once the image correction algorithm 20 has been applied to the uncorrected image 22, the data processing hardware 18 is arranged to output a corrected image 24 which contains less of the banding artefact than the uncorrected image 22. The level of banding artefact present in the corrected image 24 is undetectable by the human eye.

Figure 2:
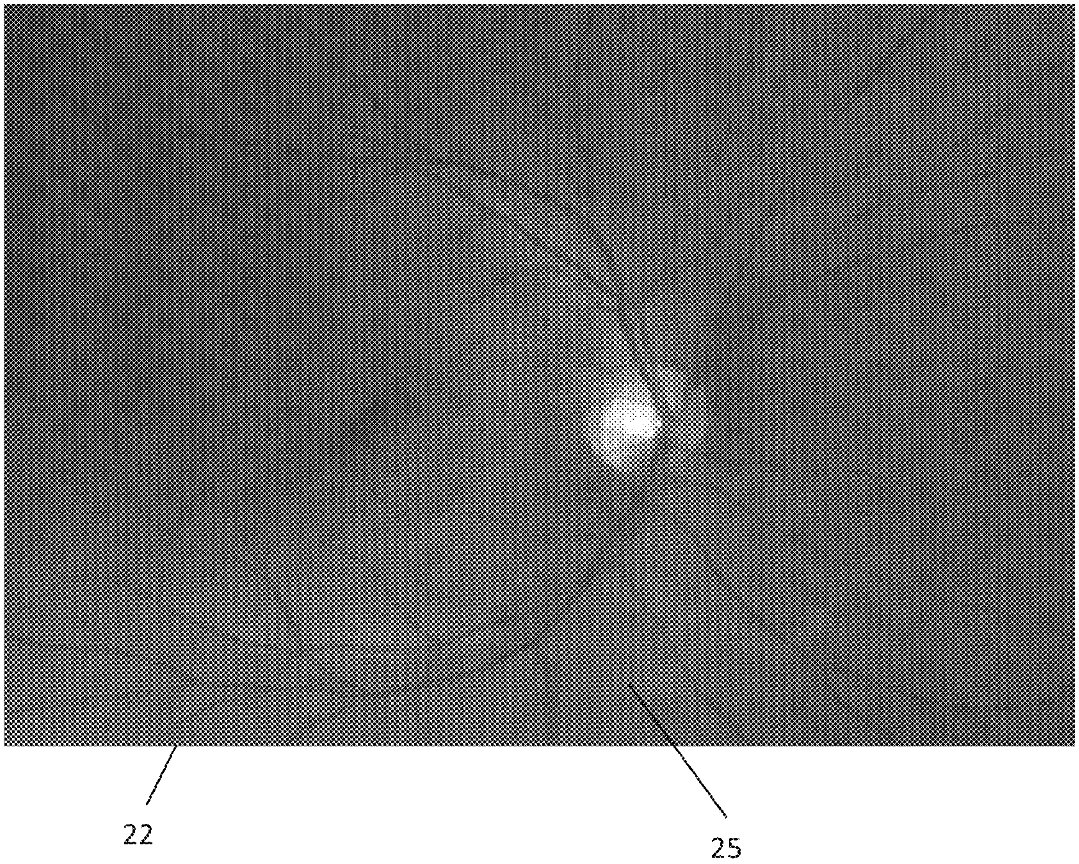
FIG. 2 is an example of an image comprising banding artefacts captured by the imaging system of FIG. 1.

Turning now to FIG. 2 there is shown an example uncorrected image 22 captured by the imaging system 10 and generated by the data processing hardware 18. The uncorrected image 22 contains vertical banding which is an example of a banding artefact 25. The banding artefact 25 may be a periodic optical aberration or a periodic line artefact, for example in the form of a set of regularly spaced linear features (bands) in the uncorrected image 22. The example uncorrected image 22 is an ophthalmic image of a retina captured by the imaging system 10 where the imaging target 11 is an eye. The banding artefact 25 in the form of vertical banding shown in the example uncorrected image 22 occurs periodically, spaced at sixteen-pixel intervals in a horizontal direction. The sixteen-pixel spacing between adjacent bands may be caused, at least in part, by variations in the reflectivity of each of the sixteen reflective facets of the polygon scanning mirror 205. In another example embodiment where the polygon scanning mirror 205 has a different number of reflective facets the spacing between adjacent bands may vary accordingly. The banding artefact 25 shown in the uncorrected image 22 detracts from the overall image quality and it is therefore desirable to remove the vertical banding from the uncorrected image 22 without compromising the quality of the image of the imaging target 11.

Figure 3:
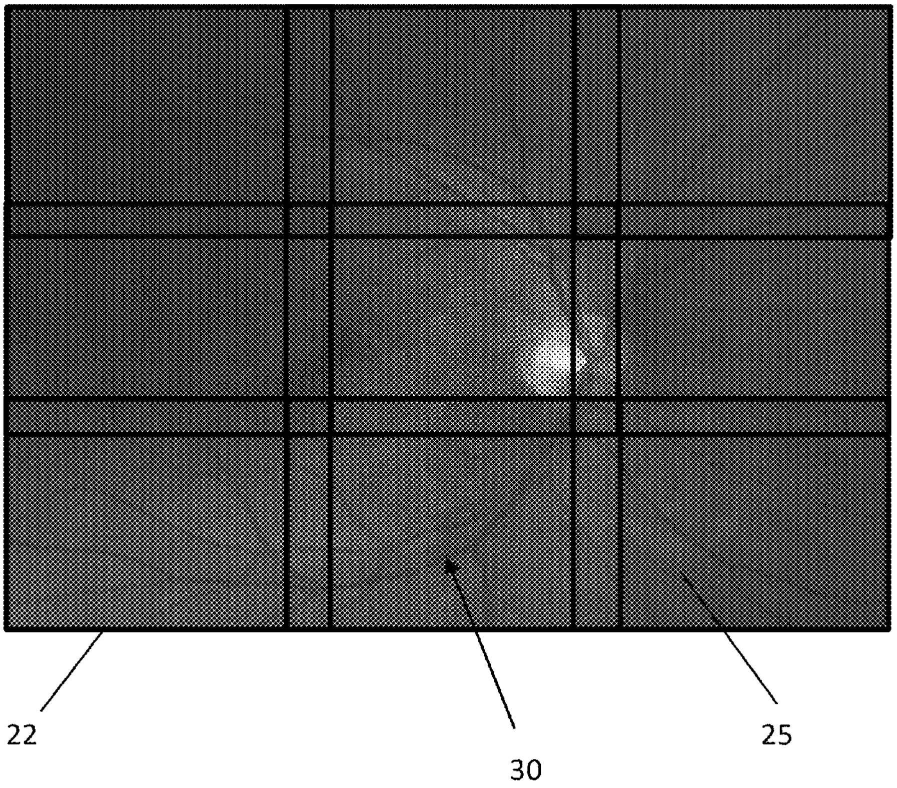
FIG. 3 is a schematic illustration of the image of FIG. 2 segmented into partially overlapping segments.

The data processing hardware 18 comprises an image correction algorithm 20 which, when executed by the data processing hardware 18, is configured to remove or suppress the banding artefact 25 present in the uncorrected image 22. The data processing hardware 18 is configured to segment the uncorrected image 22 into 2D partially overlapping segments. FIG. 3 shows an example of the uncorrected image 22 segmented into nine partially overlapping segments 30. Whilst the uncorrected image 22 has been segmented into nine partially overlapping segments 30 in FIG. 3 for clarity, the skilled reader will appreciate that in further example embodiments the image could be segmented into smaller overlapping segments. For example, the image could be segmented into a 10×10 grid, a 100×100 grid or larger depending on the severity of the banding artefact 25 and/or the size of the uncorrected image 22.

The partially overlapping segments 30 in FIG. 3 are rectangular segments of equal size that partially overlap adjacent segments 30. The level of overlap between adjacent segments 30 can be varied by the data processing hardware 18. Cases with particularly severe banding artefacts 25 may have increased overlap of segments 30 as the application of the correction algorithm 20 may introduce severe edge effects or edge artefacts that encroach further towards the centre of each segment 30 and thus more of each segment 30 must be removed to remove the edge effects or artefacts prior to recombining the corrected segments 30 to generate the corrected image 24. In the example shown in FIG. 3, the segments 30 overlap in both the horizontal and vertical directions. In another embodiment the segments 30 may overlap in only, for example, the horizontal or vertical direction.

Figure 4:
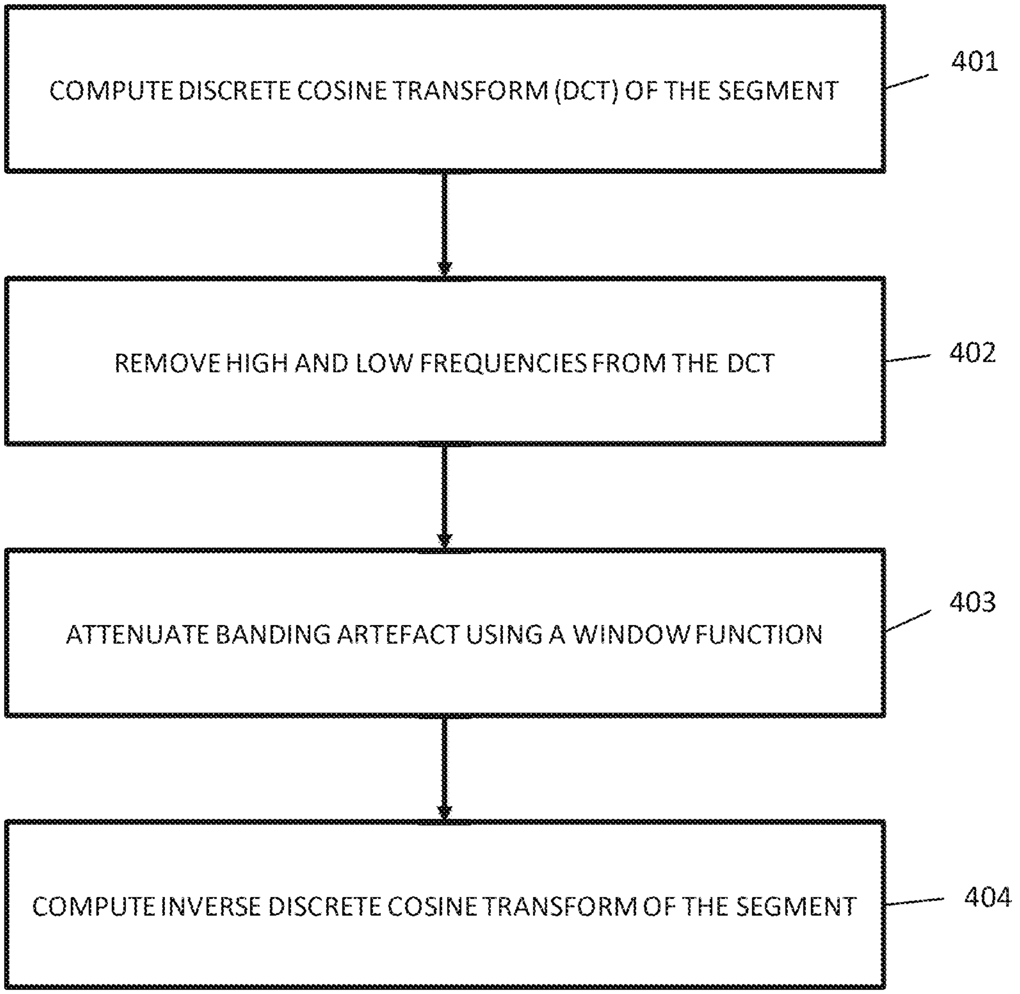
FIG. 4 is a flow chart illustrating a method of suppressing a banding artefact in one of the partially overlapping segments of FIG. 3.

Once the data processing hardware 18 has segmented the uncorrected image 22 into partially overlapping segments 30 the image correction algorithm 20 is executed by the data processing hardware 18 such that the image correction algorithm 20 is applied to each of the partially overlapping segments 30 to correct the banding artefact 25 present in each of the segments 30 individually by performing the method outlined in FIG. 4 on each segment 30 within the uncorrected image 22 as described in further detail below.

FIG. 4 is a flow chart illustrating a method of suppressing the banding artefact 25 present in each of the overlapping segments 30 in the uncorrected image 22. The method outlined in FIG. 4 may be performed by applying the correction algorithm 20 to each of the overlapping segments 30 in the uncorrected image 22 such that the method outlined in FIG. 4 is applied to each of the segments 30 in the uncorrected image 22. The skilled reader will understand that, whilst the method illustrated in FIG. 4 is described in relation to a single partially overlapping segment 30, the method may, as in the present example embodiment, be performed on every partially overlapping segment 30 present in an uncorrected image 22 to remove or suppress the banding artefact 25 present in each partially overlapping segment 30.

In Step 401 the discrete cosine transform (DCT) of a given partially overlapping segment 30 is computed. Applying the discrete cosine transform to a segment 30 converts the image contained within the segment 30 from the spatial domain to the frequency domain by defining the image as a series of cosine functions each having different frequencies that correspond to frequencies in the image. Using the discrete cosine transform to convert the image to the frequency domain opposed to another transform, such as for example the discrete Fourier transform, is beneficial as the discrete cosine transform introduces less edge effects into each segment 30 compared to the discrete Fourier transform. Furthermore, each frequency bin in the discrete cosine transform corresponds to a wider range of frequencies than a bin in the corresponding discrete Fourier transform. This is beneficial as the banding artefact 25 to be suppressed by the image correction algorithm 20 is typically a sinusoidal signal and as such the peak and/or trough of the banding artefact sinusoidal signal fits into a single bin in the discrete cosine transform thereby allowing the banding artefact 25 to be attenuated or suppressed more easily in the discrete cosine transform than would be possible in, for example, the discrete Fourier transform.

In Step 402 the high and low frequencies within the discrete cosine transform of the segment 30 are removed to create a modified discrete cosine transform of the segment 30. For example, the discrete cosine transform coefficients having an absolute value equal to or above, a threshold value of, for example 2, are removed. Removing the high and/or low frequencies may comprise setting the discrete cosine transform coefficients having an absolute value equal to or above the threshold value to zero. Removing the high and low frequencies within the discrete cosine transform of the segment 30 prevents background noise and higher frequency components in the signal from being amplified in future steps in the image correction process by the image correction algorithm 20. Furthermore, removing the high and low frequencies from each segment 30 in the frequency domain, once the discrete cosine transform has been computed, allows the high and low signals to be removed more effectively than would otherwise be possible had the frequencies been removed in the spatial domain, prior to computing the discrete cosine transform of each segment 30. Removing the high and low frequencies has the effect of flattening the image by removing background noise thereby improving the quality of the resultant corrected image 24.

In Step 403 the banding artefact 25 contained within the partially overlapping segment 30 is attenuated. Attenuating the banding artefact 25 contained within the segment 30 may be performed using a window function such as a Hanning window. The window function is centred on the frequency bin corresponding to the frequency of the banding artefact 25 contained within that segment 30. The window function may be applied to window the bin in the discrete cosine transform of each segment that corresponds to the spatial frequency of the banding artefact 25. For example, the Hanning window may be centred on a bin corresponding to the frequency associated with the banding artefact 25 occurring every sixteen pixels. Parameters of the window function can be varied to select the level of attenuation applied to the target frequency. In one example the window function may apply −10 db of attenuation to the frequency associated with the banding artefact 25 present in the partially overlapping segment 30. Using a Hanning window to attenuate the frequency associated with the banding artefact 25 opposed to a bandpass filter such as a brick wall filter is beneficial as the Hanning window introduces less ringing artefacts into the signal than a brick wall filter.

The window function used to attenuate the vertical banding in Step 403 may be a multi-stage window function. For example, a two-stage or three-stage Hanning window may be used to attenuate the vertical banding in the segment 30. The primary component of the Hanning window may be centred on the bin corresponding to the frequency of the banding artefact 25 contained within the segment 30. The window function may comprise one or more secondary components located at bins corresponding to harmonics of the primary frequency associated with the banding artefact 25 being filtered by the window function such that harmonics within the segment 30 that contribute to the presence of the banding artefact 25 in the segment 30 can be attenuated by the window function.

In Step 404 the inverse discrete cosine transform (IDCT) is computed on the segment 30 to reconstruct the image contained within the segment 30 and to generate a corrected segment. The banding artefact 25 in the reconstructed image in the corrected segment is suppressed compared to the level of banding artefact 25 present within the segment 30 of the uncorrected image 22 prior to the application of the correction algorithm 20 on the uncorrected segment. Applying the inverse discrete cosine transform to the segment 30 converts the segment 30 from the frequency domain back to the spatial domain and thereby generates a corrected segment that contains less of the banding artefact 25 than was present in the segment 30 prior to the application of the correction algorithm 20.

Figure 5:
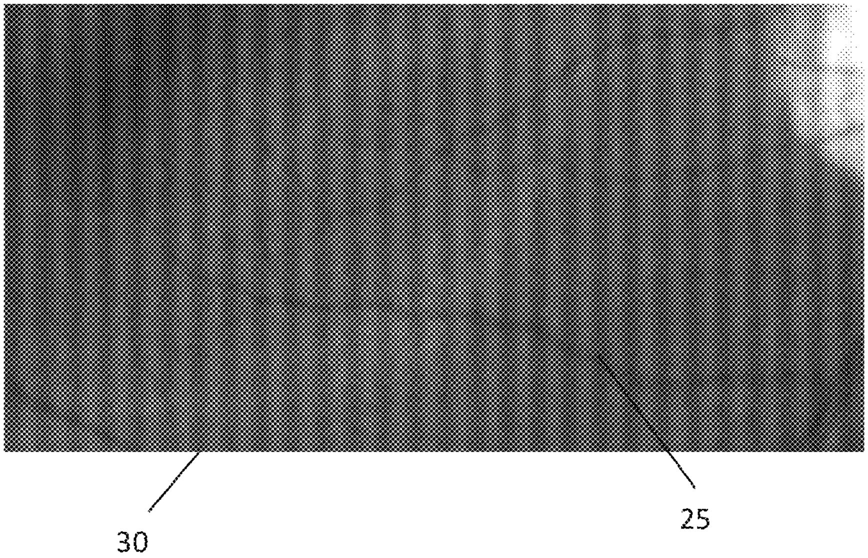
FIG. 5 is an example of a segment of the segmented image of FIG. 3 that comprises a banding artefact.
Figure 6:
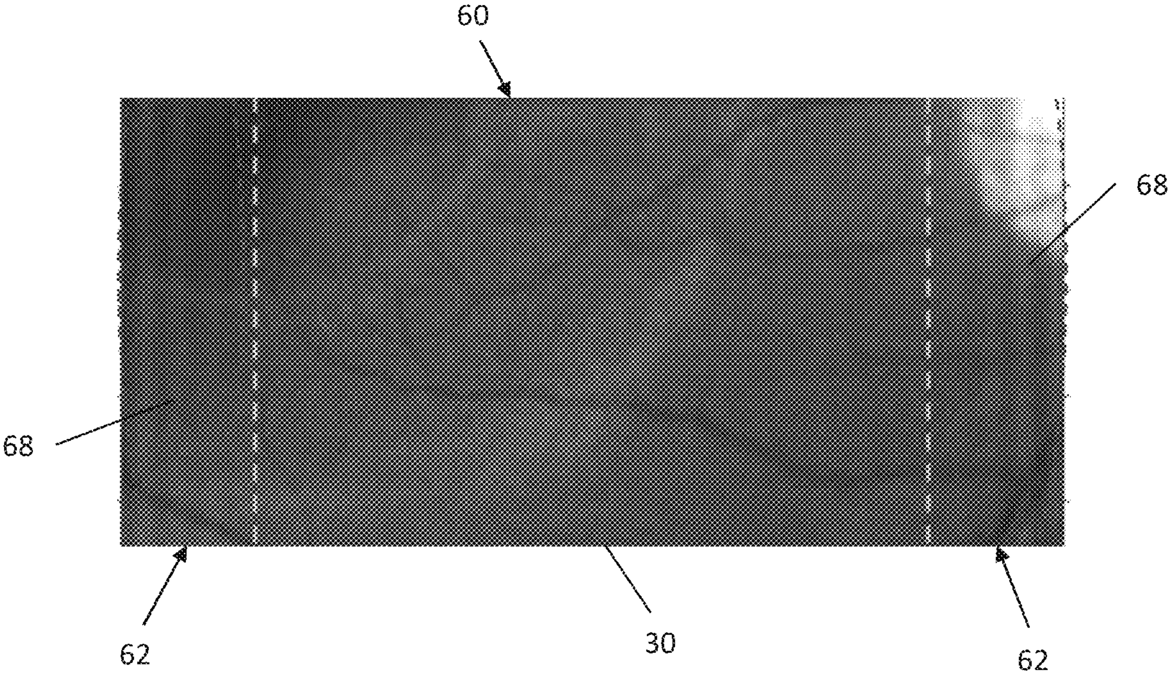
FIG. 6 is an example of the segment of FIG. 5 after a correction algorithm has been applied to the segment to suppress the banding artefact.

Turning now to FIGS. 5 and 6, an example of a segment 30 from the uncorrected image 22 before and after the application of the correction algorithm 20 is shown. FIG. 5 shows the segment 30 prior to the application of the correction algorithm 20 which is an example of an uncorrected segment. The segment 30 shown in FIG. 5 contains vertical banding that spans the width of the segment 30 with substantially uniform spacing between adjacent bands in the segment 30. In the example shown the banding appears periodically, with a period of 16 pixels. FIG. 6 shows the segment 30 after the correction algorithm 20 has been applied to the segment 30. As shown in FIG. 6, the banding artefact 25 has been suppressed sufficiently in a central portion 60 of the corrected segment 30 such that it is no longer visible in the image. However, the application of the correction algorithm 20 has resulted in the manifestation of edge effects 68 in the peripheral regions 62 of the segment 30 within which banding is still visible as a result of the edge effects 68.

As illustrated in FIG. 3, the segments 30 are dimensioned such that the edges of each segment 30 overlap. When the correction algorithm 20 is applied to a segment 30 the resulting edge effects 68 contained within the peripheral regions 62 of a given segment 30 correspond to an overlapping portion of the segment 30. As such, the peripheral regions 62 of each segment 30 can be removed or cropped such that the peripheral regions 62 containing banding artefacts as a result of edge effects 68 can be discarded. The remaining central portion 60 of each segment 30 can be recombined or stitched together to by the data processing hardware 18 to generate the corrected image 24. The central portion 60 is an example of a corrected segment. The dimensions and amount of overlapping of the segments 30 in FIG. 3 may be selected such that the peripheral regions 62 of a segment 30 that contain banding from edge effects 68 are fully contained within the overlapping regions of adjacent segments 30.

Figure 7:
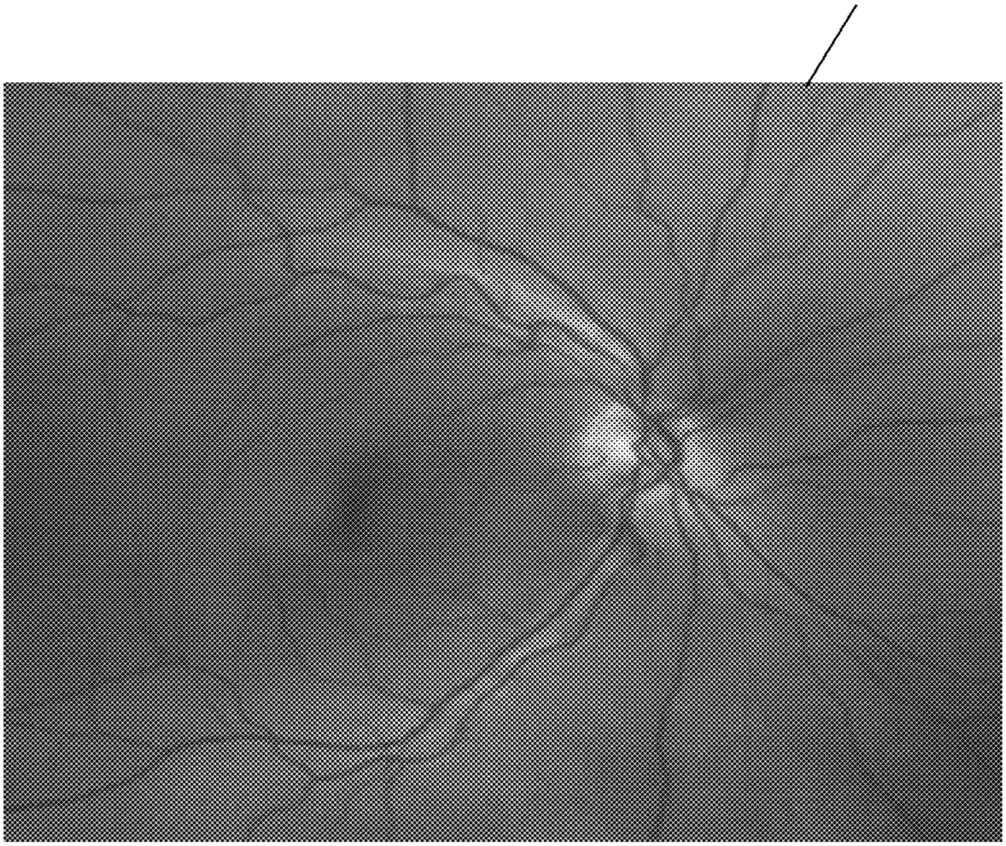
FIG. 7 is an example of an image captured by the imaging system of FIG. 1 after the banding artefacts have been suppressed according to an example embodiment herein.

FIG. 7 shows an example of a corrected image 24 that has been generated by combining the corrected segments that have been generated by applying the correction algorithm 20 to the segments 30 of the uncorrected image 22. The data processing hardware 18 is arranged to blend the corrected segments 64 together to generate the corrected image 24 such that joins between adjacent segments 30 are not visible or perceivable by the human eye. The banding in the corrected image 24 has been suppressed sufficiently (or completely eradicated) such that it is no longer visible in the corrected image 24.

Figure 8:
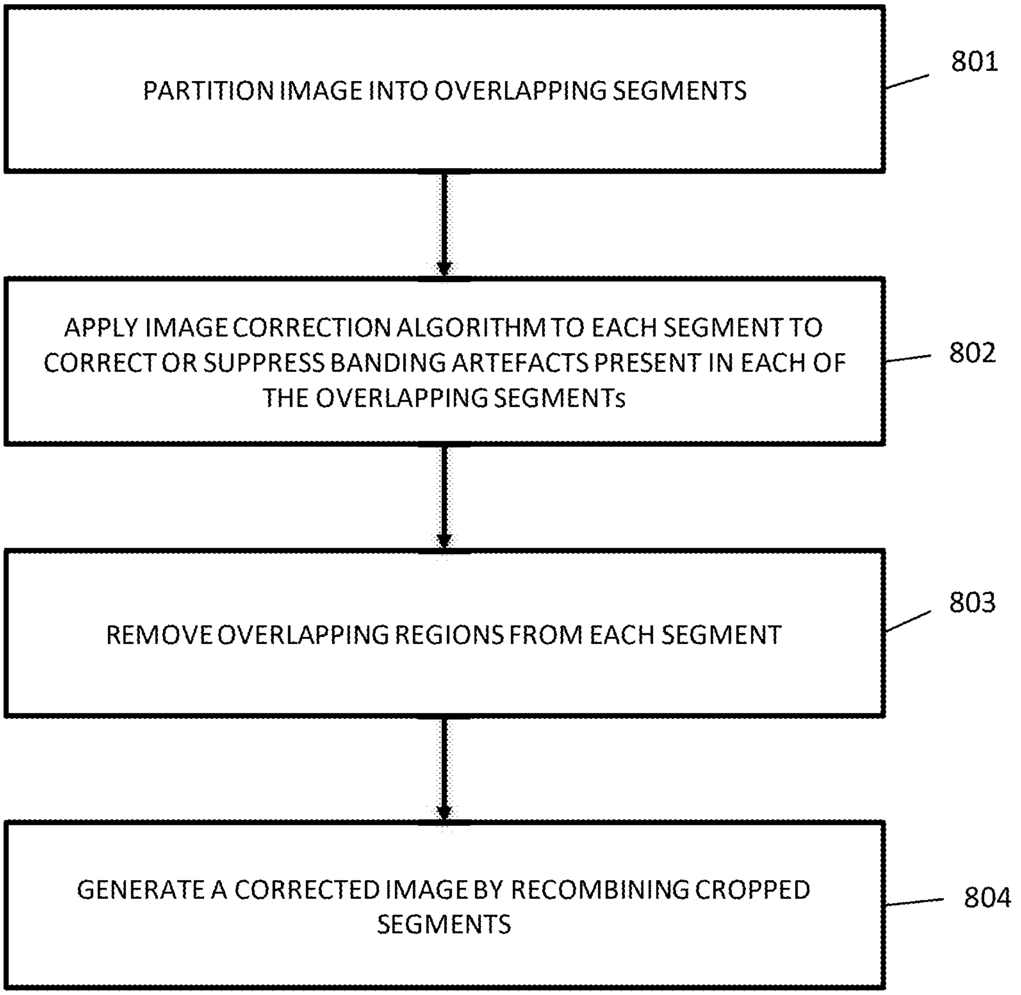
FIG. 8 is a flow chart illustrating a method of suppressing a banding artefact in an image captured by the imaging system of FIG. 1.

Turning now to FIG. 8 there is shown a flow chart illustrating a method of suppressing a banding artefact 25 in an image of an imaging target 11. The method illustrated in FIG. 8 may be performed by the data processing hardware 18 of the imaging system 10. The method may be performed on the uncorrected image 22 to generate the corrected image 24.

In Step 801 the uncorrected image 22 is partitioned into at least partially overlapping 2D segments. The number and dimension (size) of the segments 30 may be selected based on parameters such as one or more of: the severity of the banding artefacts 25 present in the uncorrected image 22, the resolution of the uncorrected image 22 and the processing power of the data processing hardware 18. The segments are typically rectangular and of equal size. Furthermore, the amount of overlapping between adjacent segments is typically equal. If the banding artefacts 25 present in the uncorrected image 22 are severe then the uncorrected image 22 may be partitioned into smaller segments such that, for example, the uncorrected image 22 is partitioned into 1000×1000 overlapping segments or greater. Increasing the number of segments 30 that the uncorrected image 22 is partitioned into generally increases the effectiveness of the application of image correction algorithm 20. However, increasing the number of segments 30 the uncorrected image is partitioned into also increases the computational time for performing the method of suppressing the banding artefact 25 in the uncorrected image 22.

Next, in Step 802 the banding artefact 25 is corrected or suppressed in each of the overlapping segments 30 by applying an image correction algorithm 20 to each of the segments 30 in the uncorrected image 22. Correcting or suppressing the banding artefact 25 present in each of the partially overlapping segments 30 may be conducted by performing the method outlined in FIG. 4 as described above. Applying the image correction algorithm 20 to each of the partially overlapping segments 20 suppresses the banding artefact 25 present in the respective partially overlapping segments 30. Applying the image correction algorithm 20 to each segment 30 comprises computing the discrete cosine transform for each of the partially overlapping segments 30.

In Step 803 at least part of the overlapping regions 62 are removed from each of the segments 30 to remove edge effects 68 or artefacts introduced into the respective segments 30 by the image correction algorithm 20 in Step 802. Removing at least part of the overlapping regions 62 may comprise cropping at least some of the peripheral region 62 from each segment 30 to remove the artefacts or edge effects 68 that have been introduced into each of the segments 30 by the image correction algorithm 20. Cropping the peripheral region 62 from the segment 30 beneficially removes artefacts and/or edge effects 68 introduced into each segment 30 by the image correction algorithm 20. Removing at least part of the overlapping regions 62 from each of the overlapping segments 30 generates a corrected segment. Removing at least part of the overlapping regions 62 may be performed after the image correction algorithm 20 has been applied to a segment 30.

In Step 804 each of the cropped segments 30 are recombined to generate the corrected image 24. Recombining the cropped segments 30 may comprise mosaicing and optionally blending the segments 30 to generate the corrected image 24. Blending adjacent segments 30 when recombining the segments 30 to generate the corrected image 24 prevents artefacts being introduced in the corrected image 24 due to misalignment of recombined segments 30. Combining each of the corrected segments 30 to generate the corrected image 24 may comprise blending and/or aligning peripheral regions of adjacent segments 30 to generate the corrected image 24 such that joins between adjacent segments 30 is not perceivable in the corrected image 24. Aligning adjacent segments may comprise identifying common features present in adjacent segments 30 and overlaying the common features in the adjacent segments 30 to align the adjacent segments 30 in the corrected image 24.

Figure 9:
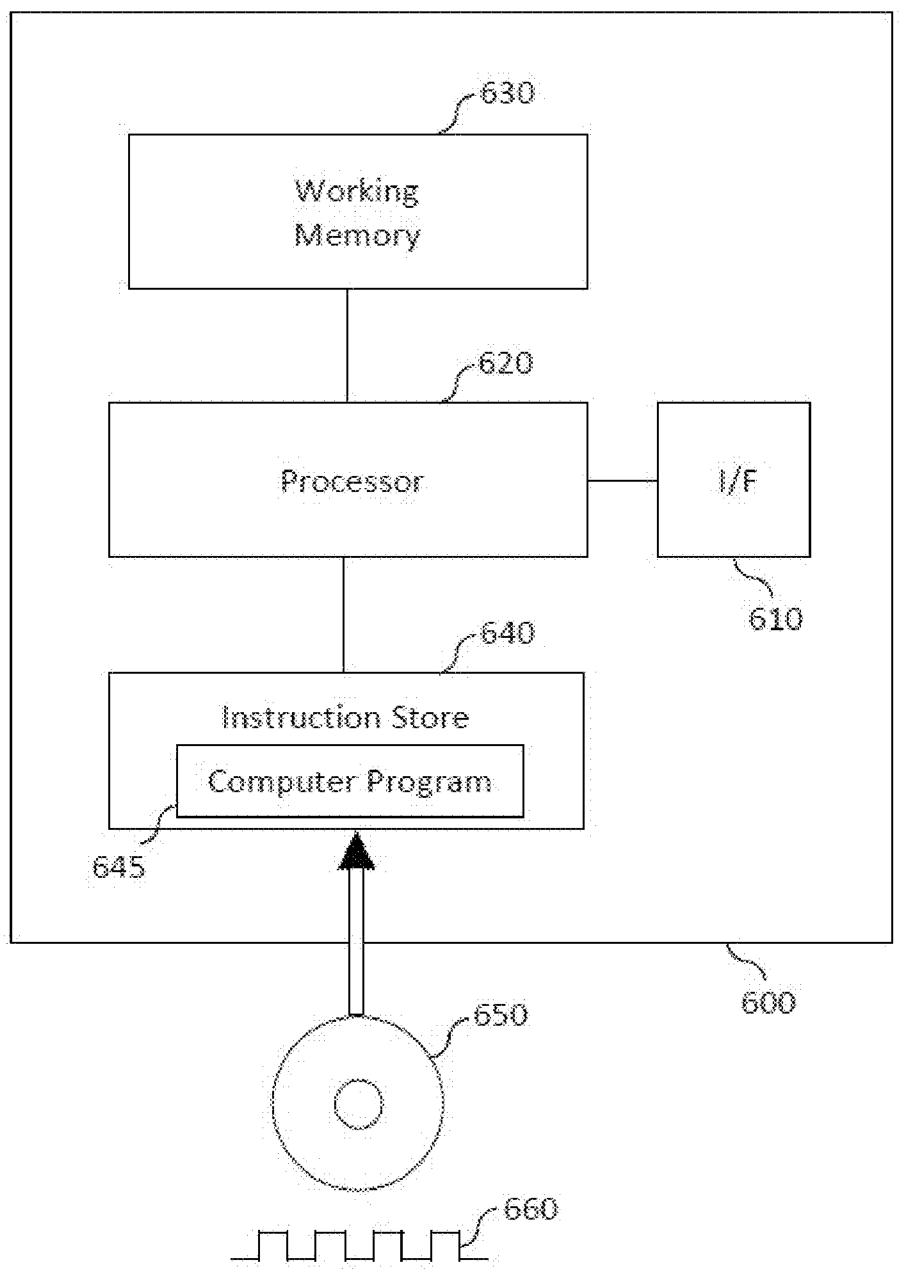
FIG. 9 is an example hardware implementation of an apparatus that can operate as the data processing hardware for an imaging system according to an example embodiment herein.

FIG. 9 is a schematic illustration of a programmable signal processing hardware 600, configured to remove or suppress a banding artefact 25 in an image captured by the imaging system 10. The programmable signal processing hardware 600 can perform at least part of the functionalities of the data processing hardware 18 of the imaging system 10, and, in one example embodiment herein, at least part of the hardware 600 is included in the data processing hardware 18. The programmable signal processing apparatus 600 comprises a communication interface (I/F) 610, for receiving a detection signal $S_d$ from the photodetector 16 and/or for outputting a corrected image 24. In one example embodiment herein, the communication interface (I/F) 610 can input/output any information obtained as part of the methods described herein.

The signal processing apparatus 600 further comprises a processor (e.g. a Central Processing Unit, CPU, and/or a Graphics Processing Unit, GPU) 620, a working memory 630 (e.g. a random access memory) and an instruction store 640 storing a computer program 645 comprising computer-readable instructions which, when executed by the processor 620, cause the processor 620 to perform various functions including those of the processor 18 in FIG. 1, and/or the functions of the methods described herein. In one example embodiment herein, only the processor 620 is included in the data processing hardware 18, although in other examples one or more additional components of the hardware 600 also are included in the data processing hardware 18 as well.

The working memory 630 stores information used by the processor 620 during execution of the computer program 645. The instruction store 640 comprises, for example, a ROM (e.g. in the form of an electrically erasable programmable read-only memory (EEPROM) or flash memory)

which is pre-loaded with the computer-readable instructions. Alternatively, the instruction store 640 comprises a RAM or similar type of memory, and the computer-readable instructions of the computer program 645 can be input thereto from a computer program product, such as a non-transitory, computer-readable storage medium 650 in the form of a CD-ROM, DVDROM, etc. or a computer-readable signal 660 carrying the computer-readable instructions. In any case, the computer program 645, when executed by the processor 620, causes the processor 620 to perform the methods described herein, including by example and without limitation, a method of suppressing a banding artefact in an ophthalmic image as described herein above.

In one example embodiment herein, the data processing hardware 18 of the example embodiments described above comprises the computer processor 620 and memory 640 storing the computer-readable instructions which, when executed by the computer processor 620, cause the computer processor 620 to perform the methods described herein, including by example and without limitation, a method of suppressing a banding artefact in an ophthalmic image acquired by an imaging system 10 as described herein. It should be noted, however, that the data processing hardware 18 may alternatively be implemented in non-programmable hardware, such as an ASIC, an FPGA or other integrated circuit dedicated to performing the functions of the data processing hardware 18 described above, or a combination of such non-programmable hardware and programmable hardware as described above with reference to FIG. 9.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

The invention claimed is:

1. A method of suppressing a banding artefact in an ophthalmic image of a patient's eye, the method comprising:

partitioning the ophthalmic image into a plurality of segments that partially overlap each other, wherein the ophthalmic image comprises the banding artefact, each segment of the plurality of segments comprises one or more overlapping regions, and each overlapping region is a region of overlap of the segment with a respective adjacent segment of the plurality of segments;

applying an image correction algorithm, which computes a discrete cosine transform of each segment of the plurality of segments, to suppress the banding artefact in the plurality of segments, the image correction algorithm introducing at least one image processing artefact into the one or more overlapping regions of each segment of the plurality of segments;

removing at least part of the one or more overlapping regions from each segment of the plurality of segments to remove the at least one image processing artefact introduced by the image correction algorithm, to generate a respective corrected segment that omits a region comprising the at least one image processing artefact; and combining the corrected segments to generate a corrected ophthalmic image that comprises less of the banding artefact than the ophthalmic image.

2. The method as claimed in claim 1, further comprising performing filtering in a frequency domain, after the discrete cosine transform has been computed, to remove at least one of low frequency signals and high frequency signals from each of the segments.

3. The method as claimed in claim 2, wherein the filtering comprises removing discrete cosine transform coefficients having an absolute value equal to or above a threshold value from each of the segments.

4. The method as claimed in claim 1, further comprising applying a window function to the computed discrete cosine transform of each segment, wherein the window function is applied to window a bin in the discrete cosine transform of each segment, which bin corresponds to a spatial frequency of the banding artefact, to attenuate the banding artefact in the discrete cosine transform of each segment.

5. The method as claimed in claim 4, wherein the window function comprises a secondary component for filtering a second frequency corresponding to a harmonic of the frequency of the banding artefact, wherein the secondary component is applied to window a bin in the discrete cosine transform of each segment corresponding to the secondary frequency.

6. The method as claimed in claim 4, wherein the window function is a Hanning window.

7. The method as claimed in claim 1, wherein applying the image correction algorithm further comprises computing, for each segment of the plurality of segments, a respective inverse discrete cosine transform of the segment after the discrete cosine transform has been computed for the segment.

8. The method as claimed in claim 1, wherein combining the corrected segments to generate the corrected ophthalmic image comprises blending a peripheral region of a first corrected segment of the corrected segments with a peripheral region of an adjacent corrected segment of the corrected segments.

9. An ophthalmic imaging system for imaging a patient's eye, the imaging system comprising:

a light source arranged to emit a light beam;

a scanning system comprising a polygon scanning mirror, wherein the polygon scanning mirror is arranged to scan the light beam over a region of the patient's eye, a photodetector optically coupled to the scanning system, wherein the photodetector is configured to generate a detection signal based on light reflected by the patient's eye; and data processing hardware configured to receive the detection signal from the photodetector and generate, based on the received detection signal, an ophthalmic image of the patient's eye, wherein the ophthalmic image comprises a banding artefact;

wherein the data processing hardware is further configured to:

partition the ophthalmic image into a plurality of segments that partially overlap each other, wherein the ophthalmic image comprises the banding artefact, each segment of the plurality of segments comprises one or more overlapping regions, and each overlapping region is a region of overlap of the segment with a respective adjacent segment of the plurality of segments;

apply an image correction algorithm, which computes a discrete cosine transform of each segment of the plurality of segments, to suppress the banding artefact in the plurality of segments, the image correction algorithm introducing at least one image processing artefact into the one or more overlapping regions of each segment of the plurality of segments;

remove at least part of the one or more overlapping regions from each segment of the plurality of segments to remove the at least one image processing artefact introduced by the image correction algorithm, to generate a corrected segment that omits a region comprising the at least one image processing artefact; and combine each of the corrected segments to generate a corrected ophthalmic image that comprises less of the banding artefact than the ophthalmic image.

10. The ophthalmic imaging system as claimed in claim 9, wherein the data processing hardware is further configured to perform filtering in a frequency domain, after the discrete cosine transform has been computed, to remove at least one of low frequency signals and high frequency signals from each of the segments.

11. The ophthalmic imaging system as claimed in claim 9, wherein the data processing hardware is further configured to apply a window function to the computed discrete cosine transform of each segment, wherein the window function is applied to window a bin in the discrete cosine transform of each segment, which bin corresponds to a spatial frequency of the banding artefact, to attenuate the banding artefact in the discrete cosine transform of each segment.

12. The ophthalmic imaging system as claimed in claim 11, wherein the window function comprises at least one of:

a secondary component for filtering a second frequency corresponding to a harmonic of the frequency of the banding artefact, wherein the secondary component is applied to window a bin in the discrete cosine transform of each segment corresponding to the secondary frequency; or a Hanning window.

13. The ophthalmic imaging system as claimed in claim 9, wherein applying the image correction algorithm further comprises computing, for each segment of the plurality of segments, a respective inverse discrete cosine transform of the segment after the discrete cosine transform has been computed for each of the partially overlapping segments.

14. The ophthalmic imaging system as claimed in claim 9, wherein combining the corrected segments to generate the corrected ophthalmic image comprises blending a peripheral region of a first corrected segment of the corrected segments with a peripheral region of an adjacent corrected segment of the corrected segments.

15. A non-transitory computer-readable storage medium comprising instructions which, when executed by a processor, cause the processor to perform a set of operations, the set of operations comprising:

partitioning an ophthalmic image into a plurality of segments that partially overlap each other, wherein the ophthalmic image comprises a banding artefact, each segment of the plurality of segments comprises one or more overlapping regions, and each overlapping region is a region of overlap of the segment with a respective adjacent segment of the plurality of segments;

applying an image correction algorithm, which computes a discrete cosine transform of each segment of the plurality of segments, to suppress the banding artefact in the plurality of segments, the image correction algorithm introducing at least one image processing artefact into the one or more overlapping regions of each segment of the plurality of segments;

removing at least part of the one or more overlapping regions from each segment of the plurality of segments to remove the at least one image processing artefact introduced by the image correction algorithm, to generate a respective corrected segment that omits a region comprising the at least one image processing artefact; and combining the corrected segments to generate a corrected ophthalmic image that comprises less of the banding artefact than the ophthalmic image.

16. The non-transitory computer-readable storage medium as claimed in claim 15, wherein the set of operations further comprises performing filtering in a frequency domain, after the discrete cosine transform has been computed, to remove at least one of low frequency signals and high frequency signals from each of the segments.

17. The non-transitory computer-readable storage medium as claimed in claim 15, wherein the set of operations further comprises applying a window function to the computed discrete cosine transform of each segment, wherein the window function is applied to window a bin in the discrete cosine transform of each segment, which bin corresponds to a spatial frequency of the banding artefact, to attenuate the banding artefact in the discrete cosine transform of each segment.

18. The non-transitory computer-readable storage medium as claimed in claim 17, wherein the window function comprises at least one of:

a secondary component for filtering a second frequency corresponding to a harmonic of the frequency of the banding artefact, wherein the secondary component is applied to window a bin in the discrete cosine transform of each segment corresponding to the secondary frequency; or a Hanning window.

19. The non-transitory computer-readable storage medium as claimed in claim 15, wherein applying the image correction algorithm further comprises computing, for each segment of the plurality of segments, a respective inverse discrete cosine transform of the segment after the discrete cosine transform has been computed for the segment.

20. The non-transitory computer-readable storage medium as claimed in claim 15, wherein combining the corrected segments to generate the corrected ophthalmic image comprises blending a peripheral region of a first corrected segment of the corrected segments with a peripheral region of an adjacent corrected segment of the corrected segments.

* * * * *